United States Patent [19]

Shih et al.

[11] Patent Number: 5,807,872
[45] Date of Patent: Sep. 15, 1998

[54] IMIDAZOYLALKYL SUBSTITUTED WITH A SIX MEMBERED NITROGEN CONTAINING HETEROCYCLIC RING

[75] Inventors: Neng-Yang Shih, North Caldwell; Michael J. Green, Skillman, both of N.J.

[73] Assignee: Schering Corporation, Kenilworth, N.J.

[21] Appl. No.: 244,830

[22] PCT Filed: Dec. 16, 1992

[86] PCT No.: PCT/US92/10698

§ 371 Date: Jun. 15, 1994

§ 102(e) Date: Jun. 15, 1994

[87] PCT Pub. No.: WO93/12107

PCT Pub. Date: Jun. 24, 1993

[30] Foreign Application Priority Data

Dec. 16, 1992 [WO] WIPO ................ PCT/US92/10698

[51] Int. Cl.$^6$ ................ A61K 31/445; C07D 401/06
[52] U.S. Cl. ................ 514/326; 546/210
[58] Field of Search ................ 546/210; 514/326

[56] References Cited

U.S. PATENT DOCUMENTS

| | | | |
|---|---|---|---|
| 3,491,098 | 1/1970 | Archer | 514/252 |
| 4,324,792 | 4/1982 | Bradshaw et al. | 514/212 |
| 4,404,382 | 9/1983 | Gall | 544/360 |
| 4,404,387 | 9/1983 | Gall | 546/193 |
| 4,431,653 | 2/1984 | Wei | 514/326 |
| 4,707,487 | 11/1987 | Arrang et al. | 514/326 |
| 4,767,778 | 8/1988 | Arrang et al. | 514/397 |
| 4,925,851 | 5/1990 | Houlihan | 514/326 |
| 4,935,417 | 6/1990 | Pascal et al. | 514/218 |
| 5,010,075 | 4/1991 | Pascal et al. | 514/218 |
| 5,071,859 | 12/1991 | Knudsen | 514/326 |
| 5,091,428 | 2/1992 | Pascal et al. | 514/252 |
| 5,290,790 | 3/1994 | Arrang et al. | 514/326 |

FOREIGN PATENT DOCUMENTS

| | | |
|---|---|---|
| 0197840 | 10/1986 | European Pat. Off. . |
| 0338939 | 10/1989 | European Pat. Off. . |
| 0372125 | 6/1990 | European Pat. Off. . |

OTHER PUBLICATIONS

West Jr. et al., Journal of Neurochemistry, vol. 55, No. 5, pp. 1612–1616 (1990).
West Jr. et al, Molecular Pharmacology, 38:610–613 (1990).
Korte et al., Biochemical and Biophysical Research Communications, vol. 168, No. 3, pp. 979–986 (1990).

*Primary Examiner*—Ceila Chang
*Attorney, Agent, or Firm*—Henry C. Jeanette

[57] ABSTRACT

Disclosed is a compound of Formula 1.0:

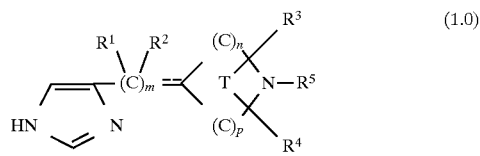

or a pharmaceutically acceptable salt or solvate thereof.

Also disclosed are pharmaceutical compositions comprising a pharmaceutically acceptable carrier and an effective amount of a Compound of Formula 1.0.

Further disclosed is a method of treating allergy (for example asthma), inflammation, hypertension, raised intraocular pressure (such as glaucoma)—i.e., a method of lowering intraocular pressure, sleeping disorders, states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula 1.0 to a patient in need of such treatment.

16 Claims, No Drawings

IMIDAZOYLALKYL SUBSTITUTED WITH A SIX MEMBERED NITROGEN CONTAINING HETEROCYCLIC RING

This application is a 371 of PCT/US 92/10698 filed Dec. 16, 1992.

BACKGROUND $H_3$ receptor sites are known and are of current interest to those skilled in the art—for example, see: West, Jr. et al., "Biexponential Kinetics of (R)-α-[$^3$H]Methylhistamine Binding to the Rat Brain $H_3$ Histamine Receptor", Journal of Neurochemistry, Vol. 55, No. 5, pp. 1612–1616, 1990; West, Jr. et al., "Identification of Two $H_3$-Histamine Receptor Subtypes", Molecular Pharmacology, 38:610–613; and Korte et al., "Characterization and Tissue Distribution of $H_3$ Histamine Receptors in Guinea Pigs by $N^\alpha$-Methylhistamine", Biochemical and Biophysical Research Communications, Vol. 168, No. 3, pp. 979–986.

Arrang et al. in U.S. Pat. No. 4,767,778 (Issued Aug. 30, 1988) disclose a pharmaceutical composition containing a histamine derivative of the formula:

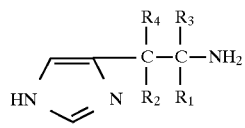

wherein each of $R_1$, $R_2$, and $R_4$, represents a hydrogen or a methyl, or $R_1$ and $R_2$ taken together represent a methylene, and $R_3$ is a hydrogen, a methyl or a carboxy, with the proviso that $R_1$, $R_2$, $R_3$, and $R_4$ are not simultaneously methyl groups. It is disclosed that the derivatives behave as complete agonists of the $H_3$ receptors in rat brain and produce a maximal inhibition of release identical to that induced by histamine (approximately 60%). It is also disclosed that the histamine derivatives powerfully inhibit the release and synthesis of histamine by very selectively stimulating the $H_3$ receptors. Consequently, according to Arrang et al., the derivatives are likely to decrease histaminergic transmission in the digestive tract and in the nervous, cardiovascular and immune systems. Arrang et al. disclose that the derivatives can be used in therapy as a drug having sedative effects, as a sleep regulator, anticonvulsant, regulator of hypothalamo-hypophyseal secretion, antidepressant, and modulator of cerebral circulation. According to Arrang et al., inhibition of the release of inflammation messengers in various allergic conditions (e.g., asthma) is expected to result from stimulation of the $H_3$ receptors of the lung. It is further disclosed that the inhibition of release of gastric histamine is likely to exert antisecretory and antiulcerative effects. According to Arrang et al., modification of release of the messengers of immune responses is likely to modulate the latter responses.

EP 0 338 939 discloses compounds of the formula:

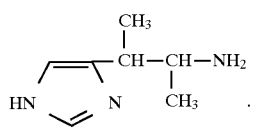

Derwent abstract 86-273706(42 for EP 0 197 840 discloses imidazole derivatives of the formula:

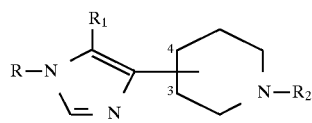

wherein $R_1$ is H, methyl or ethyl; R is H or $R_2$; and $R_2$ is 1–6C alkyl, piperonyl, 3-(benzimidazolon-1-yl)propyl, —CZ—NHR$_5$ or a group (i):

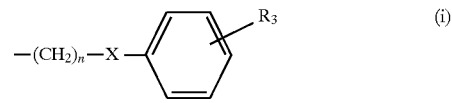

wherein n is 0–3; X is a bond, O, S, NH, CO, CH=CH or a group (ii):

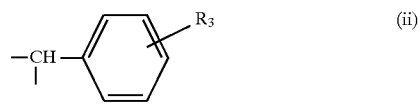

$R_3$ is H, methyl, halo, CN, $CF_3$ or $COR_4$; $R_4$ is 1–6C alkyl, 3–6C cycloalkyl or phenyl (optionally substituted by methyl or F); Z is O, S, NH, N-methyl or N—CN; and $R_5$ is 1–8C alkyl, 3–6C cycloalkyl (optionally substituted by phenyl), 3–6C cycloalkyl(1–3C)alkyl, phenyl (optionally substituted by methyl, halo or $CF_3$), phenyl(1–3C)alkyl, naphthyl, adamantyl or p-toluenesulphonyl. It is disclosed that these compounds are psychotropic agents. It is also disclosed that these compounds antagonise the histamine H3 receptors and increase the speed of cerebral histamine renewal.

Derwent abstract 90184730/24 for U.S. Pat. No. 4,925,851 discloses 2- or 4-(2-(1H-imidazol-1-yl)ethyl) piperidine compounds useful as antitumour agents for inhibiting lymphoma, sarcoma, myeloma and leukaemia. The compounds have the formula:

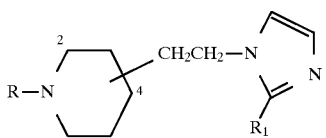

wherein R is —CH$_2$(CH$_2$)$_m$—Me, —CO—(CH$_2$)$_m$—Me or —CO—CMe$_2$—R$_2$; m is 2–18; R$_2$ is H or Me; R$_1$ is —(CH$_2$)$_n$—R$_3$; n is 0–13; R$_3$ is H, i-Pr or t-Bu; and the floating group is at the 2- or 4- position; with the proviso that (1) the sum of C atoms in $R_1$ does not exceed 13; and (2) the sum of C atoms in R and $R_1$ does not exceed 25.

Derwent abstract 90-180087/24 for EP 372125A discloses compounds of the formula:

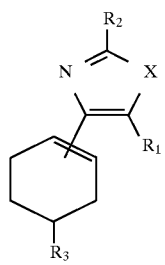

wherein X is O or S; $R_1$ is halo, $CF_3$, CN, $NO_2$, OH, or 1–6C alkoxy; $R_2$ is H, 1–6C alkyl, aryl, 7–13C aralkyl, optionally substituted amino or 5- or 6-membered N-containing ring;

and $R_3$ is 1–6C hydrocarbyl, 7–13C aralkyl or 1–13C acyl. It is disclosed that these compounds have alpha2-antagonist activity with no dopamine activity and that they are useful for treating depression and other related illnesses (e.g., anxiety or cognitive disorders).

Derwent abstract 88-309195/44 for U.S. Pat. No. 4,935,417 discloses compounds of the formula:

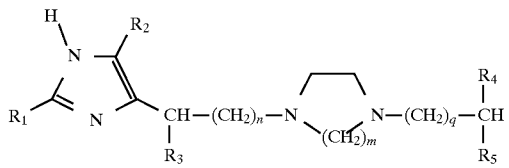

wherein (according to U.S. Pat. No. 4,935,417) $R^1$ is aryl, lower alkyl, cycloalkyl or hydrogen; $R^2$ is aryl, lower alkyl or hydrogen; $R^3$ is lower alkyl, hydroxy or hydrogen; $R^4$ is aryl or hydrogen; $R^5$ is aryl or hydrogen; m is two or three; n is zero, one or two, provided that when $R^3$ is hydroxy, n is one or two; and q is zero, one, two or three. U.S. Pat. No. 4,935,417 discloses that these compounds are calcium channel antagonists useful for treating mammals having a variety of disease states, such as stroke, epilepsy, hypertension, angina, migraine, arrhythmia, thrombosis, embolism and also for treatment of spinal injuries Compounds known in the art include:

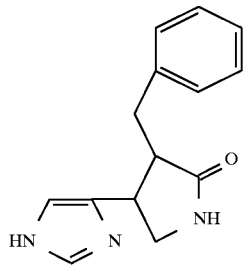

RN 85651-90-7
CA98(23):194919y

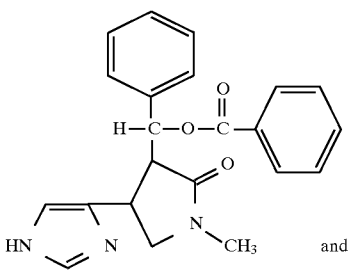

RN 81345-39-3
CA96(17):139642m

-continued

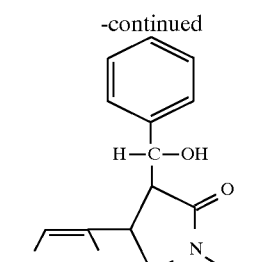

RN 81345-38-2
CA96(17):139642m

Known compounds in the art also include compounds of the formula:

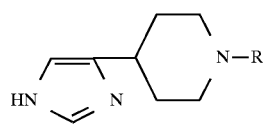

wherein R (Table 1) is:

TABLE 1

| NO. | R | RN | CA |
|---|---|---|---|
| 1 | —$CH_3$ | 106243-44-1 | 106(11):84602r |
| 2 | —$CH(CH_3)_2$ | 106243-45-2 | 106(11):84602r |
| 3 | H | 106243-23-6 | 106(11):84602r |
| 4 | —$C(S)NHC(CH_3)_2CH_2C(CH_3)$ | 106243-93-0 | 106(11):84602r |
| 5 | —$C(O)NHCH(CH_3)$(phenyl) | 106243-90-7 | — |
| 6 | —$C(S)NH$(p-chlorophenyl) | 106243-85-0 | — |
| 7 | —$C(O)NH$(phenyl) | 106243-77-0 | — |
| 8 | —$C(NH)N(CH_3)$(cyclopropyl) | 106243-73-6 | — |
| 9 | —$C(S)NHCH_3$ | 106243-61-2 | — |
| 10 | —$CH_2CH_2$-phenyl | 106243-49-6 | — |
| 11 | —$CH_2CH_2$-p-flurophenyl | 106243-67-8 | — |
| 12 | benzyl | 106243-25-8 | — |

Additionally known compounds include:

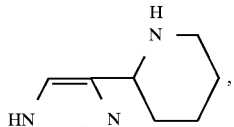

RN 51746-84-0
CA80(15):82801a

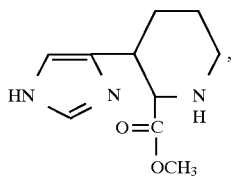

RN 67319-35-1
CA89(13):109229v

-continued

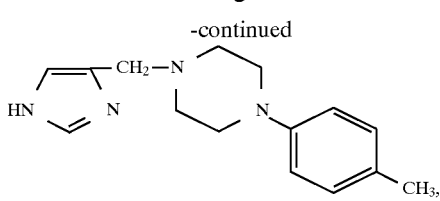

RN 58013-30-2
CA89(23):197598t
CA84(9):59553v

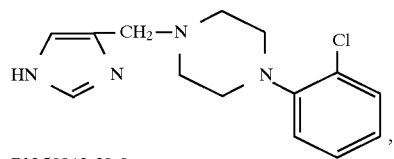

RN 58013-29-9
CA89(23):197598t
CA84(9):59553v

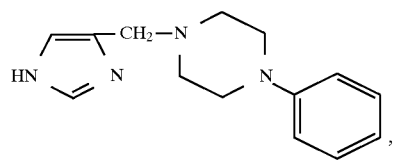

RN 58013-24-4

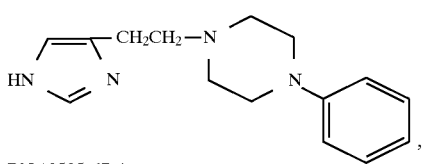

RN 18505-67-4
CA72(17):90459v
CA69(3):10467w

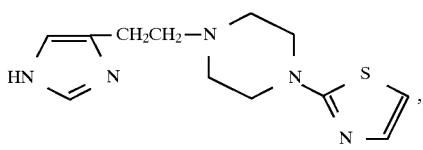

RN 46906-54-1

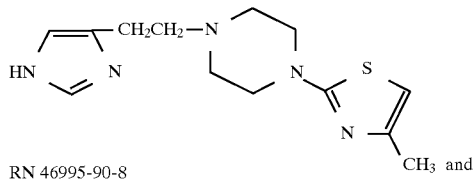

RN 46995-90-8

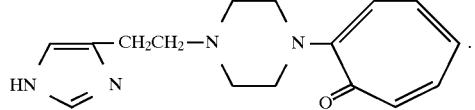

RN 80101-09-3
CA96(1):6760b

In view of the art's interest in compounds which effect the $H_3$ receptors, novel compounds having agonist or antagonist activity on $H_3$ receptors would be a welcome contribution to the art. This invention provides just such a contribution by providing novel compounds having $H_3$ agonist or antagonist activity.

SUMMARY OF THE INVENTION

This invention provides compounds of the formula:

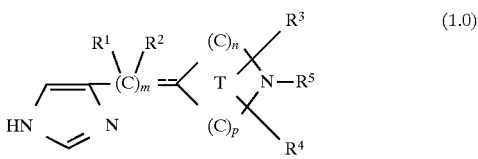

or a pharmaceutically acceptable salt or solvate thereof, wherein:

(A) m is an integer selected from the group consisting of: 1 and 2;

(B) n and p are integers and are each independently selected from the group consisting of: 0, 1, 2, 3, and 4 such that the sum of n and p is 4 and T is a 6-membered ring;

(C) $R^3$ and $R^4$ are each independently bound to the same or different carbon atom of ring T such that there is only one $R^3$ group and one $R^4$ group in ring T, and each $R^1$, $R^2$, $R^3$, and $R^4$ is independently selected from the group consisting of:

(1) H;

(2) $C_1$ to $C_6$ alkyl; and (3) $-(CH_2)_q-R^6$ wherein q is an integer of: 1 to 7, and $R^6$ is selected from the group consisting of: phenyl, substituted phenyl, $-OR^7$, $-C(O)OR^7$, $-C(O)R^7$, $-OC(O)R^7$, $-C(O)NR^7R^8$, CN and $-SR^7$ wherein $R^7$ and $R^8$ are as defined below, and wherein the substituents on said substituted phenyl are each independently selected from the group consisting of: $-OH$, $-O-(C_1$ to $C_6)$alkyl, halogen, $C_1$ to $C_6$ alkyl, $-CF_3$, $-CN$, and $-NO_2$, and wherein said substituted phenyl contains from 1 to 3 substituents;

(D) $R^5$ is selected from the group consisting of:

(1) H;

(2) $C_1$ to $C_{20}$ alkyl;

(3) $C_3$ to $C_6$ cycloalkyl;

(4) $-C(O)OR^{7'}$; wherein $R^{7'}$ is the same as $R^7$ defined below except that $R^{7'}$ is not H;

(5) $-C(O)R^7$;

(6) $-C(O)NR^7R^8$;

(7) allyl;

(8) propargyl; and (9) $-(CH_2)_q-R^6$, wherein q and $R^6$ are as defined above, and when q is equal to 1, then $R^6$ is not OH or SH;

(E) $R^7$ and $R^8$ are each independently selected from the group consisting of: H, $C_1$ to $C_6$ alkyl, and $C_3$ to $C_6$ cycloalkyl;

(F) the dotted line (------) represents a double bond that is optionally present when m is 1, and n is not 0, and p is not 0 (i.e., the nitrogen in the ring is not bound directly to the carbon atom bearing the double bond), and when said double bond is present then $R^2$ is absent; and (G) when m is 2, each $R^1$ is the same or different substituent for each m, and each $R^2$ is the same or different substituent for each m, and at least two of the substituents $R^1$ and/or $R^2$ are H.

Those skilled in the art will appreciate that the total number of substituents on each of the $-(C)_n-$ and $-(C)_p-$ groups is two, and that such substituents are independently selected from the group consisting of hydrogen, $R^3$ and $R^4$, such that there is a total of only one $R^3$ and one $R^4$ substituent in ring T.

This invention also provides pharmaceutical compositions comprising a pharmaceutically acceptable carrier and an effective amount of a Compound of Formula 1.0.

This invention further provides a method of treating allergy, (for example asthma), inflammation, hypertension, states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula 1.0 to a patient in need of such treatment.

DETAILED DESCRIPTION OF THE INVENTION

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms;

halogen (halo)—represents fluoro, chloro, bromo or iodo;

DMF—stands for (N,N-dimethylforamide);

LDA—stands for lithium diisopropylamide;

PDC—stands for pyridinium dichromate;

proton sponge—stands for [1,8-bis(dimethylamino)-naphthalene, N,N,N',N'-tetramethyl-1,8-naphthalenediamine];

SEM—stands for 2-(trimethylsilyl)ethoxymethyl;

THF—stands for tetrahydrofuran; and

TMEDA—stands for N,N,N',N'-tetramethylethylenediamine.

Also, unless stated otherwise, the substituents for the various embodiments described below are as defined for Formula 1.0.

Preferably, for compounds of Formula 1.0, m is 1; $R^5$ is selected from the group consisting of H and $C_1$ to $C_{15}$ alkyl; and $R^1$ to $R^4$ are each independently selected from the group consisting of: H, $C_1$ to $C_6$ alkyl, and $—(CH_2)_q—R^6$ wherein $R^6$ is phenyl. Most preferably, $R^5$ is selected from the group consisting of H and $C_1$ to $C_6$ alkyl with H and methyl being even more preferable; and $R^3$ and $R^4$ are each independently selected from the group consisting of: H and methyl.

Representative compounds of this invention include compounds of the formula:

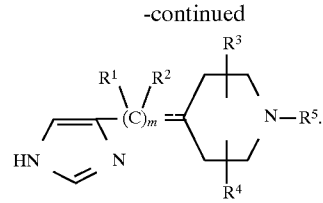
(2.0)

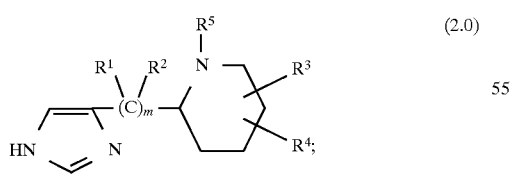
(3.0)

-continued

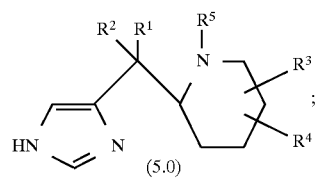
(4.0)

Representative compounds of Formula 1.0 include compounds of the Formula:

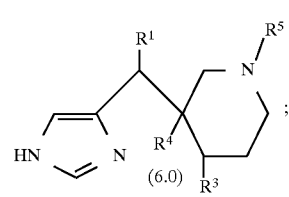
(5.0)

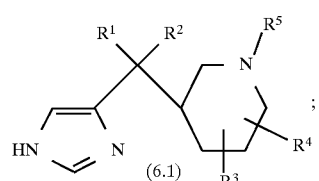
(6.0)

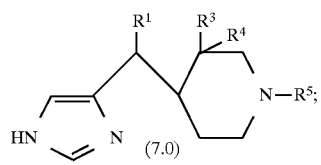
(6.1)

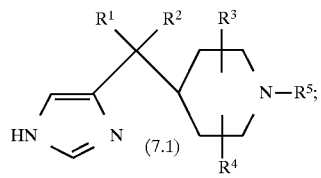
(7.0)

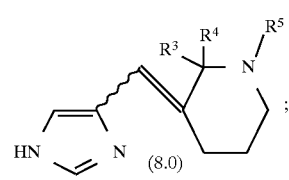
(7.1)

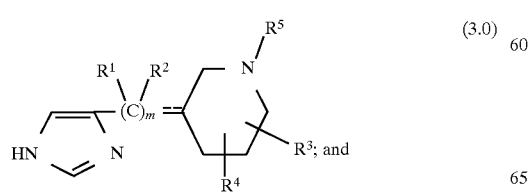
(8.0)

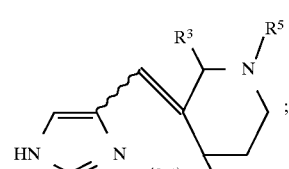
(8.1)

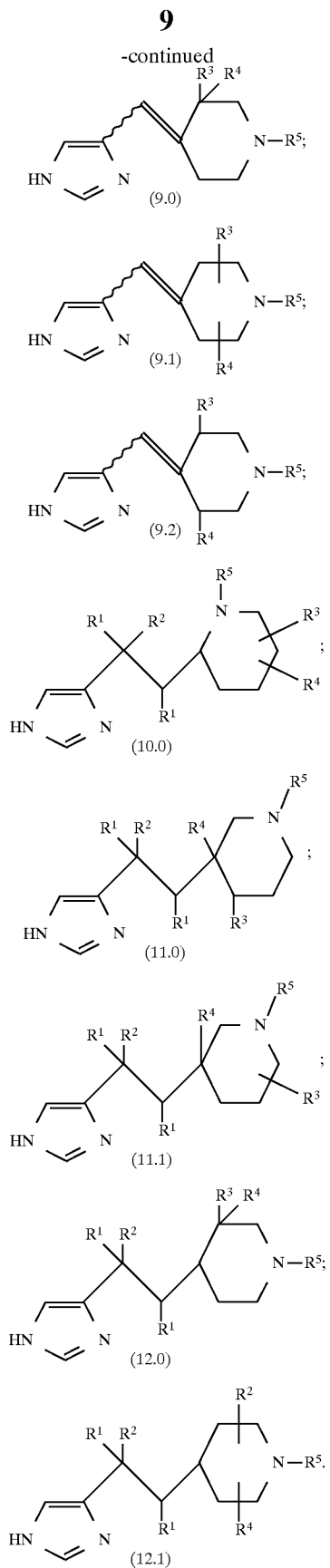
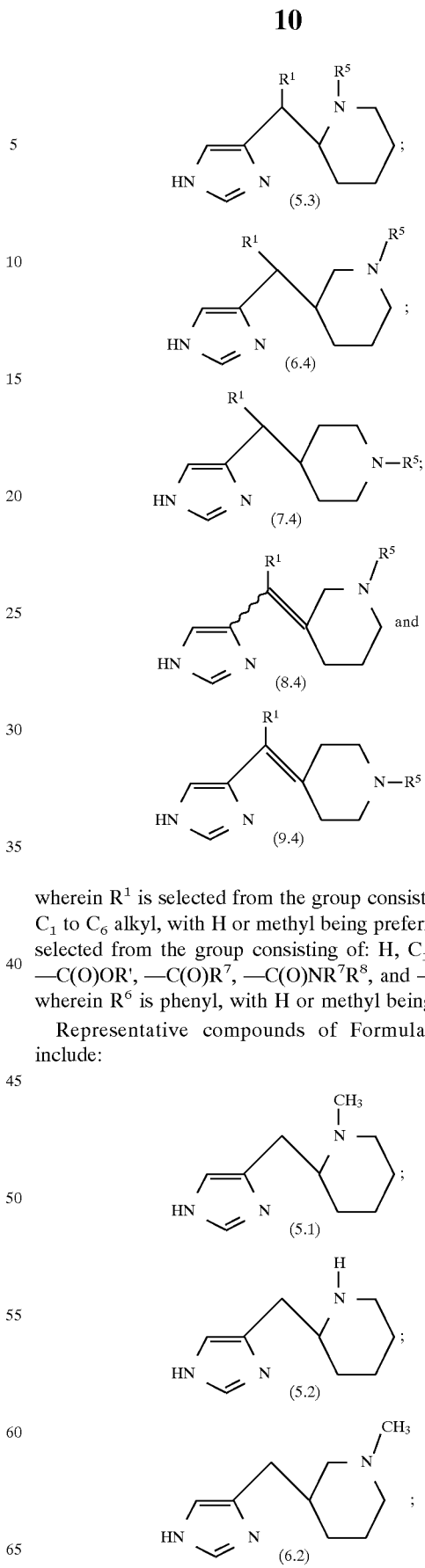

wherein $R^1$ is selected from the group consisting of: H and $C_1$ to $C_6$ alkyl, with H or methyl being preferred, and $R^5$ is selected from the group consisting of: H, $C_1$ to $C_6$ alkyl, —C(O)OR', —C(O)$R^7$, —C(O)N$R^7R^8$, and —(CH$_2$)$_q$—$R^6$ wherein $R^6$ is phenyl, with H or methyl being preferred Representative compounds of Formula 1.0 further include:

Representative compounds of Formula 1.0 also include compounds of the Formula:

-continued

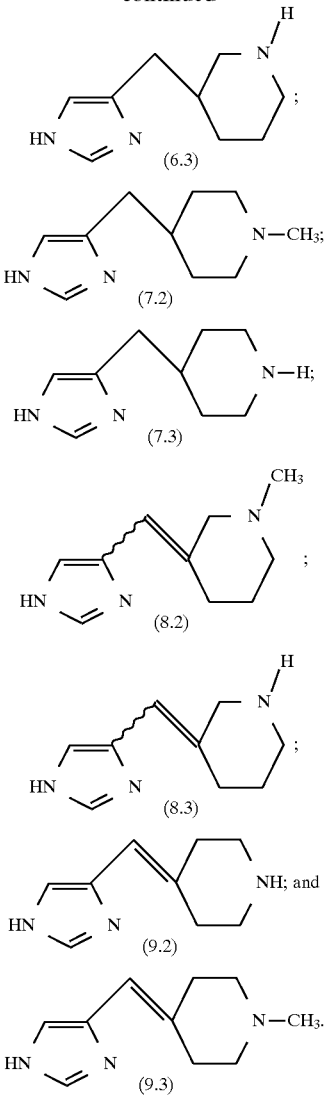

Certain compounds of the invention may exist in different isomeric (e.g., enantiomers and diastereoisomers) forms. The invention contemplates all such isomers both in pure form and in admixture, including racemic mixtures. Enol forms are also included.

The compounds of Formula 1.0 can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following processes may be employed to produce compounds of Formula 1.0. Unless stated otherwise, reactions are conducted at an appropriate temperature which allows the reaction to proceed at a reasonable rate to completion.

A PREPARATION OF COMPOUNDS WHEREIN
m IS 1, n IS 0 AND p is4

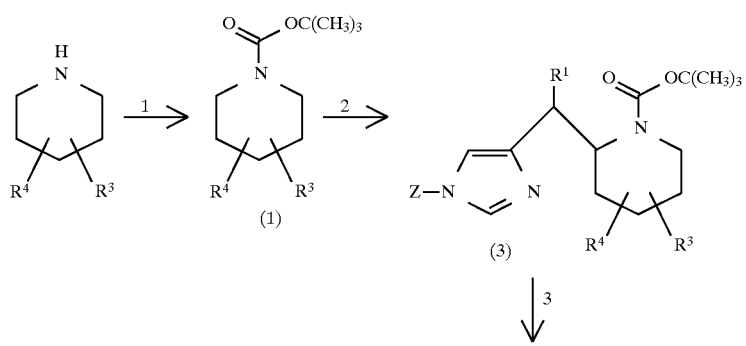

-continued

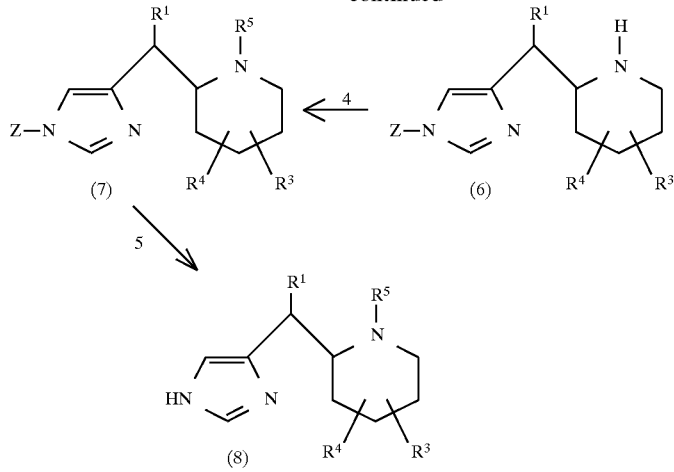

In Step 1 of Scheme 1, piperidine is reacted with di-tert-butyl dicarbonate ((tBOC)₂O) in an organic solvent optionally in the presence of an organic base. The reaction is conducted at a temperature of about 0 to about 30° C. Preferably, methylene chloride is used as the organic solvent, but other suitable organic solvents include DMF and the like. Triethylamine is used as the organic base. Other bases which can be used include 4-dimethylaminopyridine and the like. In compound (1), the t-BOC group is chosen as an activating group on nitrogen which increases the kinetic acidity of the α-proton such that a lithio salt would result upon treatment with a strong organic base (for example, Step 2). Other activating groups on nitrogen, known in the art that can also be employed include nitroso, phosphoryl, hindered acyl, and formamidine. (See Aldrichimica Acta, Vol. 8, No. 3, 1985).

In Step 2 of Scheme 1, the anion of compound (1) is reacted with compound (2)

(2)

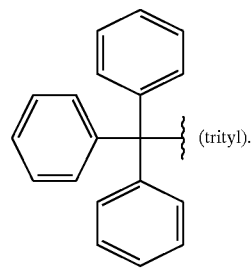

to produce compound (3). The reaction is conducted in an inert organic solvent containing an organic base and TMEDA (N,N,N',N'-tetramethylethylenediamine). The reaction is conducted at a temperature of about −78° to about 25° C. (room temperature). Tetrahydrofuran is preferably used as the solvent, other suitable solvents include diethyl ether and the like. The anion of (1) is prepared by treatment of (1) with sec-butyl-lithium in THF at −78° C.

Z represents the protecting group (trityl).

Z can be other protecting groups, such as 2-(trimethylsilyl)ethoxymethyl, benzyloxycarbonyl and the like; however, unless stated otherwise, Z preferably represents the trityl group in the process described below for making the compounds of this invention.

Those skilled in the art will appreciate that other protecting groups known in the art may be used—such as, for example, base sensitive groups wherein the protected compounds would be deprotected using basic conditions (e.g., NaOH). The processes described herein wherein the protected compound is deprotected under acidic conditions may also be carried out under basic conditions when a base sensitive protecting group is used.

Compound (2) is prepared in two steps from compound (4):

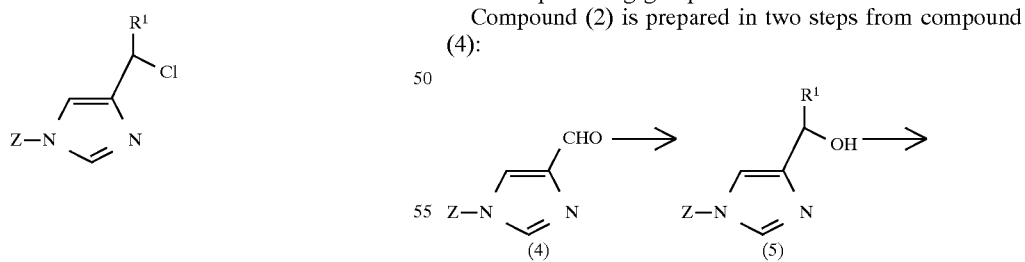

Compound (4) is reacted with an organometallic reagent R¹M, wherein M is Li or MgBr, to produce compound (5).

The reaction takes place in an inert organic solvent at a temperature of about −78° C. to 0° C. Suitable inert organic solvents include: THF, diethyl ether and the like. Compound (5) is then reacted with thionyl chloride in an inert organic solvent, such as benzene or $CH_2Cl_2$, in the presence of base to generate compound (2). The reaction is conducted at a temperature of about −20° C. to 80° C. Suitable bases include: pyridine, triethylamine, and the like. Preferably, triethylamine is used as the amine base. Compound (4) can be obtained by following the literature procedure set forth in J. K Kelly, et al., J. Med. Chem., 20, 721 (1977).

In Step 3 of Scheme 1, compound (3) is treated with HCl or similar acid in an inert organic solvent such as ethyl acetate or dioxane, at a temperature of about 0° C. to selectively deprotect (3) thus producing compound (6).

In Step 4 of Scheme 1, compound (6) may be reacted with (i) $R^5$—X (when $R^5$ is —C(O)$R^7$, —C(O)O$R^7$, —C(O)N$R^7R^8$ or alkyl) in an organic solvent optionally in the presence of a suitable base (e.g., triethylamine); or (ii) $R^{5A}$—CHO (when $R^5$ is alkyl, cycloalkyl, allyl, propargyl, benzyl or substituted benzyl) in the presence of $NaBH_3(CN)$ (sodium cyanoborohydride) or other hydrogenating conditions (e.g. $H_2$/Pd/ROH) in an organic solvent; to produce compound (7). $R^{5A}$ represents an $R^5$ group that has one less —$CH_2$— group. Preferably, $CH_2Cl_2$ is used as the solvent when $R^5$—X is used, and tetrahydrofuran is used as the solvent when $R^{5A}$—CHO is used. X represents a suitable leaving group such as Cl, Br, I, or —$OCH_3$. The reaction ((i) or (ii)) can be performed at a temperature within the range of about −30° to about 80° C. Compound (7), when $R^5$ is —C(O)N$R^7$H, may be prepared by reacting compound (6) with O=C=N—$R^7$ in an organic solvent, such as $CH_3CN$ or toluene. The reaction is performed at a temperature in the range of about 20 to reflux. Compound (6), or compound (7) wherein $R^5$ is —C(O)O(t-butyl), can be reacted with aqueous acid (e.g., HCl, HBr, and the like), at a temperature of about 25° to about 100° C., to produce compound (8) wherein $R^5$ is H.

Compound (7), wherein $R^5$ is —C(O)O$R^7$, may be reacted with NH$R^7R^8$ in an organic solvent at a temperature of about 25° to about 100° C. to form a compound of (7) wherein $R^5$ is —C(O)N$R^7R^8$. The suitable organic solvents include THF, toluene, DMF and the like.

In Step 5 of Scheme 1, compound (7) may be deprotected by treatment with dilute aqueous acid, such as HCl or HBr, at a temperature of about 70° to about 90° C. to produce compound (8). Other protecting groups are removed by methods well known in the art.

Alternatively compound (3) of Preparation A can be prepared from compounds (1) and (4) according to Scheme 2:

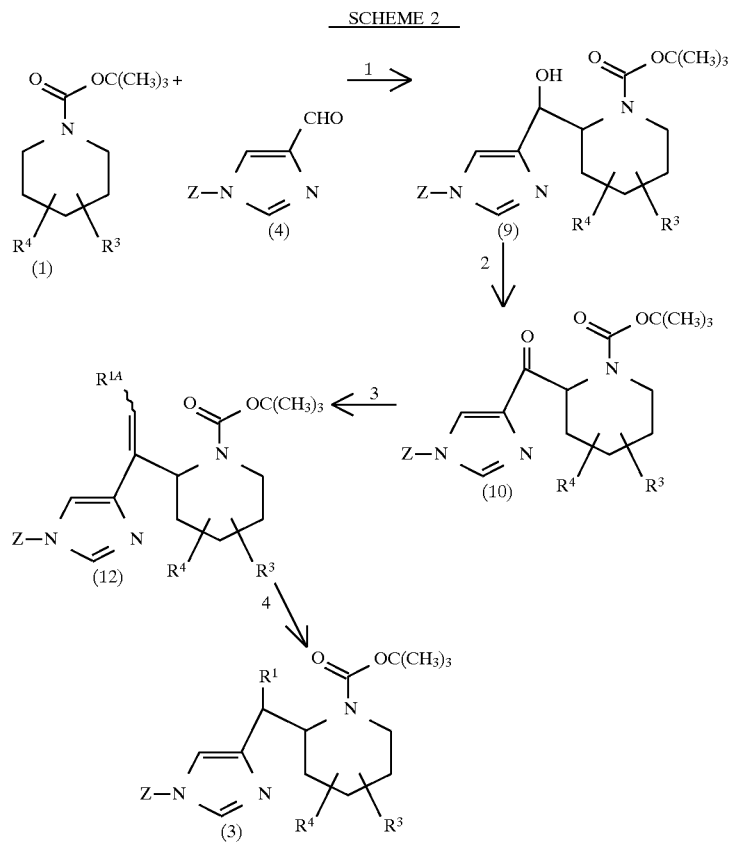

SCHEME 2

In Step 1 of Scheme 2, compound (1)—see Step 1 of Scheme 1—is reached with compound (4) in accordance with the procedure set forth in Step 2 of Scheme 1.

In Step 2 of Scheme 2, compound (9) is oxidized to produce compound (10). The oxidation is accomplished by treating compound (9) with an oxidizing agent, such as $MnO_2$ or PDC (pyridinium dichromate), in an organic solvent, such as tetrahydrofuran or methylene chloride, at a temperature of about 20° to about 80° C.

In Step 3 of Scheme 2, compound (10) is reacted, under usual Wittig reaction conditions, with compound (11)

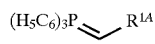

(11)

B. PREPARATION OF COMPOUNDS WHEREIN m IS 1, n IS 1 AND p is 3

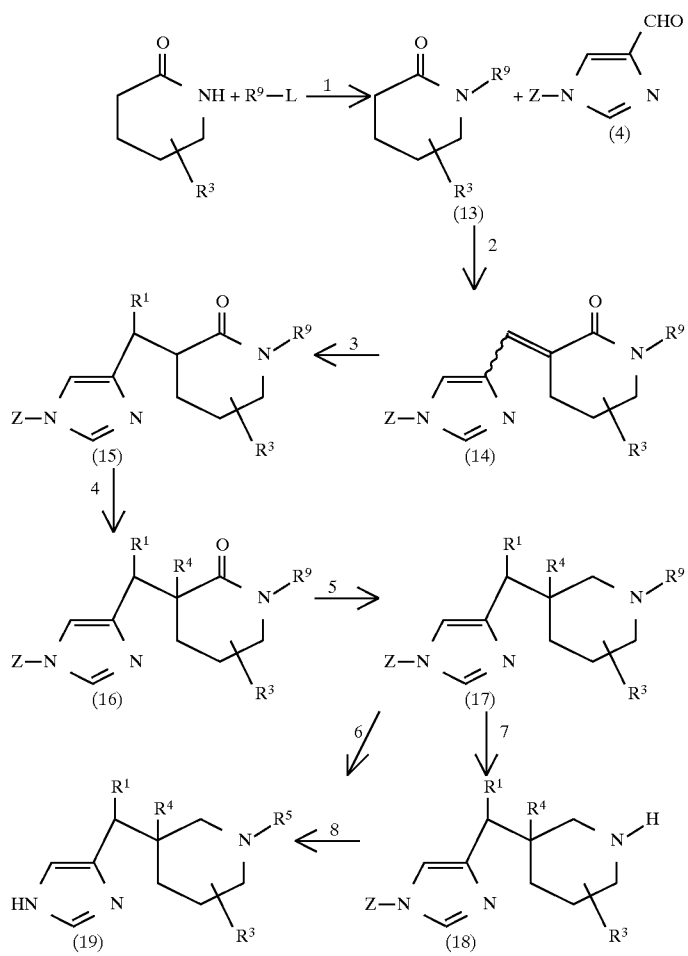

in an organic solvent at a temperature of about 25° to about 80° C. to produce compound (12). Preferably, the organic solvent is tetrahydrofuran; however, other suitable solvents, such as 1,4-dioxane and the like, can be used. In compound (11), $R^{1A}$ represents an $R^1$ group which has one less —$CH_2$— group.

In Step 4 of Scheme 2, compound (3) is produced when compound (12) is hydrogenated in THF with $H_2$ using a Pd-C (palladium/carbon) catalyst. Other organic solvents which can be used include ethyl acetate, methanol and the like. Other suitable metals such as Pt, Pd—$Al_2O_3$, Ra—Ni, NiB, and Pd—$CaCO_2$ can also be employed as the hydrogenation catalyst.

In all the preparations that follow, intermediate compounds wherein the imidazole nitrogen is protected by Z and the nitrogen of the cyclic six membered amine is substituted with —C(O)O(t-butyl) or unsubstituted, i.e., hydrogen is bound to the amine nitrogen, such as in compounds (7) or (6), respectively, such intermediate compounds can be reacted with aqueous acid (e.g., HCl, HBr, and the like), at a temperature of about 25° to about 100° C., to produce deprotected final products wherein $R^5$ is H, e.g., compound (8).

In Step 1 of Scheme 3, α-valerolactam is reacted with $R^9$—L to place the $R^9$ on the indicated nitrogen atom in compound (13). $R^9$ can either be $Si(CH_3)_2C(CH_3)_3$ or other protecting group, or $R^9$ can be an alkyl, cycloalkyl, benzyl, substituted benzyl, allyl, or propargyl group. In the latter, $R^9$ is the same as $R^5$. L is a leaving group, such as Cl, Br, I or —$OSO_2CF_3$. The reaction is conducted in an organic solvent such as THF, diethyl ether or 1,4-dioxane in the presence of a suitable base, such as lithium diisopropylamide (LDA), KH or NaH. The reaction takes place at a temperature within the range of about −78° to about 80° C.

In Step 2 of Scheme 3, the anion of compound (13) is reacted with compound (4) in an organic solvent, containing an organic base, at a temperature of about −78° to about 25° C. to produce compound (14). Suitable organic solvents include tetrahydrofuran and the like. Preferably, the organic base used to generate the anion of (13) is lithium diisopropylamide or $MN[Si(CH_3)_3]_2$ wherein M is a metal cation such as Li, Na, or K Z is trityl or other suitable protecting group.

In Step 3 of Scheme 3, compound (14) is reacted with $R^1$—Q, wherein Q is Li or MgBr, in tetrahydrofuran containing CuCN and a Lewis acid, such as $BF_3 \cdot (C_2H_5)_2O$, $(CH_3)_3SiCl$ and the like, to produce compound (15). The reaction is conducted at a temperature of about −78° to about 20° C. Tetrahydrofuran is the preferred organic solvent; however, other suitable solvents include diethyl ether and the like.

Compound (15) in Scheme 3 can alternatively be prepared by reacting an anion of compound (13) with compound (2) (see Step 2 of Scheme 1) in the presence of an organic base. Inert organic solvents, such as THF, 1,4-dioxane and the like can be employed. Preferably, the organic base used to generate the anion of (13) is lithium diisopropylamide or $MN[Si(CH_3)_3]_2$ wherein M is a metal cation such as Li, Na, or K. The reaction takes place at a temperature of about −78° C. to about 25° C.

In Step 4 of Scheme 3, the enolate of compound (15) is reacted with $R^4$—L in an inert organic solvent to produce compound (16). The reaction can be conducted at a temperature of about 0° to about 50° C. L is a suitable leaving group such as Cl, Br, I and the like. Preferably, KH is used as the base to form the enolate, but other suitable bases include LDA and the like. Suitable organic solvents include THF, 1,4-dioxane and the like. Preferably, THF is used.

In Step 5 of Scheme 3, compound (16) is reduced with $LiAlH_4$ at a temperature of about 0° to about 65° C. to produce compound (17). The reduction is conducted in tetrahydrofuran, 1,4-dioxane and the like; however, THF is preferable. Other suitable reducing agents include $BH_3$ (borane) and the like.

Step 6 of Scheme 3 (compound (17) to (19)), is followed when $R^9$ is the desired substituent on the nitrogen, such as alkyl, cycloalkyl, benzyl, substituted benzyl, allyl, or propargyl. Step 7 of Scheme 3 (compound (17) to (18)), is followed when $R^9$ is —$Si(CH_3)_2C(CH_3)_3$.

In Step 6 of Scheme 3, compound (17), when $R^9$ is alkyl, cycloalkyl, benzyl, substituted benzyl, allyl or propargyl, is deprotected following the procedure in Step 5 of Scheme 1 to produce compound (19). Alternatively, in Step 7 of Scheme 3, compound (17) is treated with tetrabutylammonium fluoride in tetrahydrofuran at a temperature of about 0° to about 50° C. to produce compound (18).

In Step 8 of Scheme 3, the procedures in Steps 4 and 5 of Scheme 1 are followed so that compound (18) is converted to compound (19).

C. PREPARATION OF COMPOUNDS WHEREIN m IS 1, n IS 1 AND p is 3

SCHEME 4

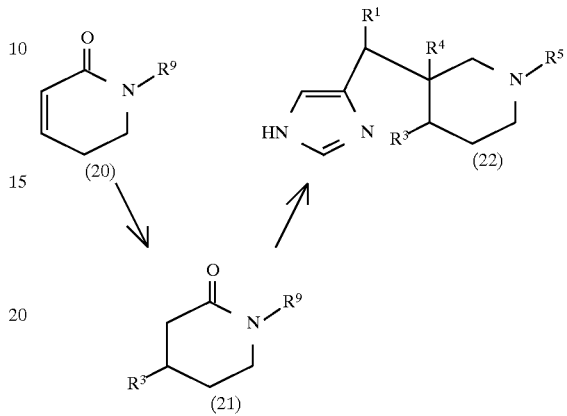

Compound (20) is reacted with $R^3$—M (wherein M is Li, ZnBr or MgBr) in tetrahydrofuran containing $BF_3 \cdot (C_2H_5)_2O$ and CuCN at a temperature of about −78° to about 20° C. to produce compound (21). Other suitable solvents such as diethyl ether can be used. Compound (21) is then converted to compound (22) in accordance with the reaction steps set forth in Scheme 3.

D. PREPARATION OF COMPOUNDS WHEREIN m IS 1 n IS 2 AND p is 2

SCHEME 5

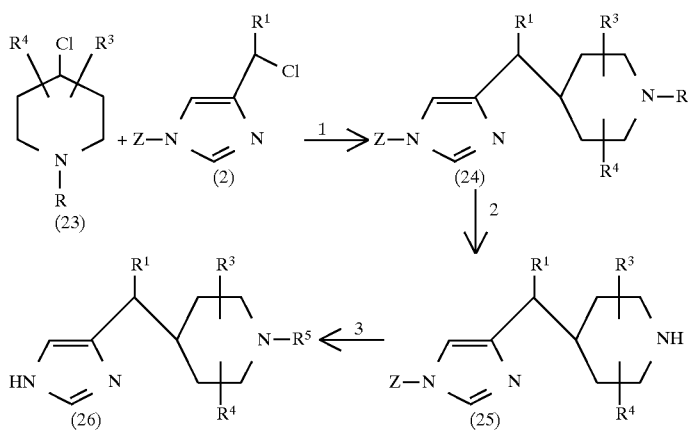

In Step 1 of Scheme 5, compound (23), wherein R is $CH_3$ or $CH_2$—$C_6H_5$, is reacted with Mg in an inert organic solvent, such as THF, at a temperature of about 50° to about 70° C. to form the Grignard reagent. The Grignard reagent is then coupled with compound (2), in the presence of CuI or CuCN, to produce compound (24). This coupling reaction is conducted at a temperature of about −78° to about 20° C. THF is the preferable solvent; however, other solvents such as 1,4-dioxane and diethyl ether can be used.

In Step 2 of Scheme 5, compound (24), wherein R is $CH_3$, is demethylated to produce compound (25) by following the literature procedures set forth either in the J. Am. Chem. Soc., 110, 8256 (1988) or in the J. Org. Chem., 49, 2081 (1984). For example, the latter procedure compound (24) is reacted with $ClC(O)OCHClCH_3$ in 1,2-dichloroethane at about 0° to about 85° C. in the presence of proton sponge to produce compound (25). Alternatively, compound (24), wherein R is $CH_2$—$C_6H_5$, is converted to compound (25) under either the hydrogenation conditions or transfer-hydrogenation conditions. For the former, the reaction is conducted in THF using Pd—C as catalyst, at a temperature of about 20° to about 70° C. Other organic solvents which can be used include ethanol and the like. Other suitable metals such as Pt, Pd—$Al_2O_3$ and the like can also be employed as catalysts. For the latter, the source of hydrogen is ammonium formate ($NH_4COO$), the catalyst is Pd/C, at a temperature of about 20° to about 80° C. The suitable organic solvents include methanol, ethanol and the like.

In Step 3 of Scheme 5, compound (25) is converted to compound (26) in accordance with the procedure set forth in Step 4 and 5 of Scheme 1.

Compound (26), wherein $R^5$ is $CH_3$ or $CH_2$—$C_6H_5$, can be directly prepared from compound (24), by a simple deprotection of the Z group, by following the procedure set forth in Step 5 of Scheme 1.

E PREPARATION OF COMPOUNDS WHEREIN m IS 1. n IS 2 AND p is 2

SCHEME 6

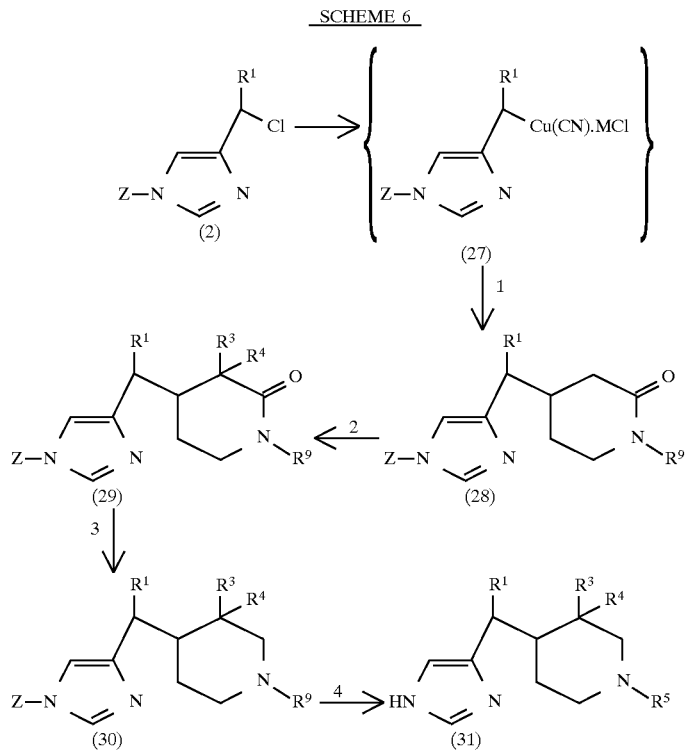

In Step 1 of Scheme 6, compound (2) is reacted with a metal (M=Zn or Mg) in an inert organic solvent, such as THF and the like, at a temperature of about −20° to about 60° C., to generate either an organozinc reagent (when M=Zn) or a Grignard reagent (when M=Mg). This organometallic reagent is then reacted with $CuCN.2LiCl$ in THF to form an intermediate, compound (27), which is subsequently coupled with compound (20), in the presence of $BF_3.(C_2H_5O)_2$ or $(CH_3)_3SiCl$, to form compound (28). This coupling reaction is conducted in an inert organic solvent, such as THF, 1.4-dioxane or diethyl ether, at a temperature of about −78° to 50° C.

In Step 2 of Scheme 6, the anion of compound (28) is reacted with $R^3$—X and then with $R^4$—X to produce compound (29). X represents a suitable leaving group, such as Cl, Br, I or —$OSO_2$—$CF_3$. Each reaction to place each substituent group on the ring takes place in an organic solvent using an organic base. THF is the solvent usually used; however, other suitable solvents include 1,4-dioxane, diethyl ether and the like. Examples of organic bases include lithium diisopropylamide, $MN[Si(CH_3)_3]_2$, KH and like. M represents a suitable metal cation such as Na, Li, K, and the like. The reaction is usually conducted at a temperature of about −78° to about 80° C.

In Step 3, compound (29) is reduced to compound (30) in accordance with the procedure set forth in Step 5 of Scheme 3.

In Step 4, the procedure in Step 6 or Steps 7 and 8 of Scheme 3 can be followed so that compound (30) is converted to compound (31).

F. PREPARATION OF COMPOUNDS WHEREIN m IS 1, n IS 2 AND p is 2

SCHEME 7

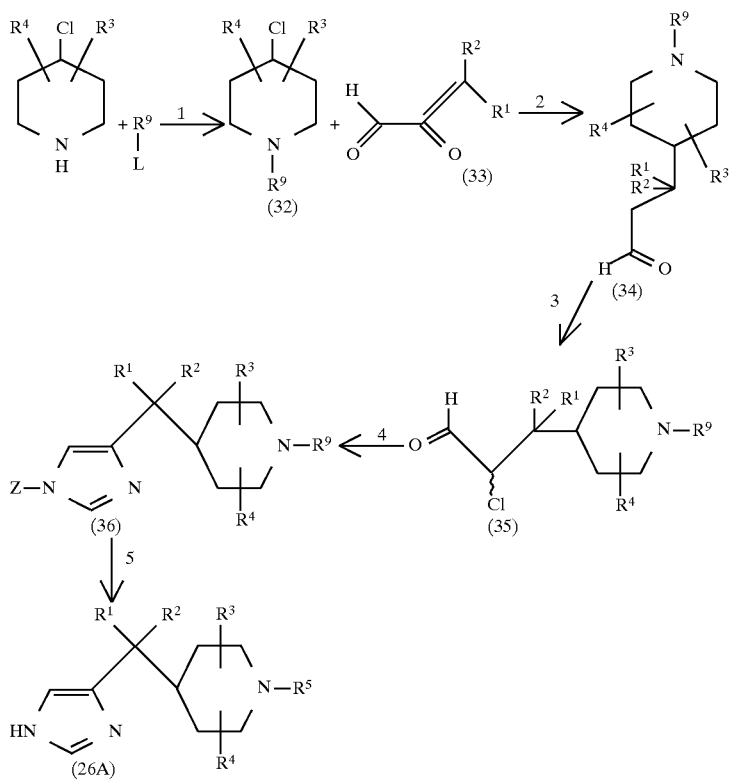

In Step 1 of Scheme 7, 4-chloropiperidine is reacted with $R^9$—L to place an $R^9$ on the nitrogen atom of compound (32). Both $R^9$ and L are as defined above in Step 1 of Scheme 3. The reaction is conducted in an organic solvent, such as THF, methylene chloride and the like, in the presence of a suitable base, such as triethylamine or 4-dimethylamino pyridine. The reaction takes place at a temperature within the range of about 0° to about 70° C.

In Step 2 of Scheme 7, compound (32) is converted to compound (34) in accordance with the reaction conditions set forth for the conversion of compound (23) to compound (24) (See Step 1 of Scheme 5).

In Step 3 of Scheme 7, compound (34) is chlorinated with sulfuryl chloride to form compound (35). This reaction is conducted at a temperature of about 0° to about 50° C. in an inert organic solvent and in the presence of suitable base. Dichloromethane is the preferred solvent, other solvents such as 1,2-dichloroethane can also be used. Suitable organic bases include triethylamine, 4-dimethylaminopyridine and the like.

In Step 4 of Scheme 7, the conversion of compound (35) to compound (36) is achieved in a two step sequence. First, compound (35) is reacted with formamide at about 175° C. (See Chem. Ber., Vol. 86, p. 88 (1953)) to form the imidazole ring. In the next step, the imidazole is protected with a Z group by reacting the product of the first step with Z-L in the presence of an organic base to give compound (36). L is a leaving group, such as Cl or Br, and Z is as defined above in Step 2 of Scheme 1. Suitable organic solvents for the protection step include methylene chloride, dimethylformamide and the like. Suitable organic bases include triethylamine and the like. The reaction may be performed at a temperature of about 0° to about 50° C.

In Step 5 of Scheme 7, compound (36) is converted to compound (26A) in accordance with the sequence set forth in Step 6 or Steps 7 and 8 in Scheme 3.

G. PREPARATION OF COMPOUNDS WHEREIN m IS 1, n IS 2 AND p is 2

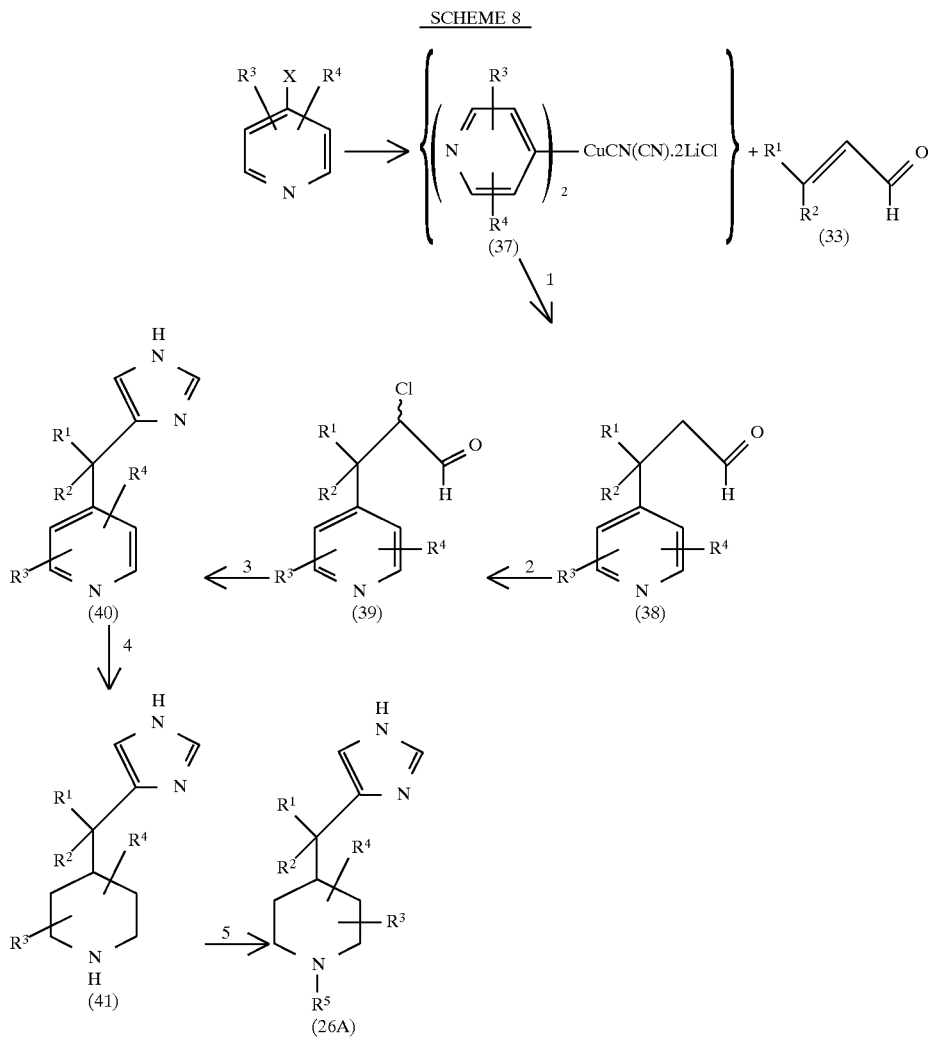

SCHEME 8

In Step 1 of Scheme 8, 4-halopyridine (wherein X is Cl, Br or I) is converted to the corresponding organocuprate reagent (37) by reaction with butyllithium and then with CuCN in an inert organic solvent at a temperature of about −78° to about 0° C. Suitable organic solvents include THF, diethylether and the like. The organocuprate (37) thus formed is then coupled with the α,β-unsaturated aldehyde (33) to form compound (38). The coupling reaction is performed at a temperature of −78° C. to 20° C. in THF in accordance with the procedure set forth in Step 1 of Scheme 6.

In Step 2 of Scheme 8, compound (38) is reacted with sulfuryl chloride, in accordance with the procedure set forth in Step 3 of of Scheme 7, to give compound (39).

In Step 3 of Scheme 8, compound (39) is then converted to compound (40) using the Bredereck Reaction conditions (See Chem. Ber., 86, 88 (1954)).

In Step 4 of Scheme 8, compound (40) is hydrogenated to compound (41), under a hydrogen pressure of about 1 to about 100 atmospheres, in the presence of suitable catalyst and in an acidic aqueous solvent. Suitable hydrogenation catalysts include Pd-black or Rh/C and the like. Suitable solvents include 10% aqueous hydrochloric acid, or 10% aqueous sulfuric acid, or the like. The reaction takes place at a temperature of about 20° to about 100° C.

In Step 5 of Scheme 8, compound (41) is converted to compound (26A) in accordance with the procedure set forth in Step 4 of Scheme 1.

H. PREPARATION OF COMPOUNDS WHEREIN m IS 1, n IS 1 AND p is 3

SCHEME 9

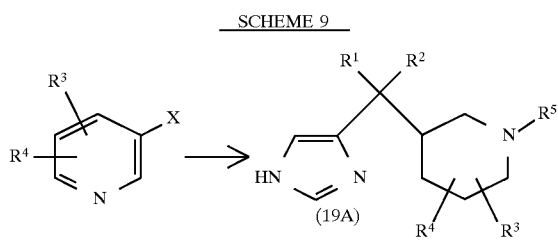

By following the reaction sequence set forth in Scheme 8, compound (19A) is prepared by starting with the 3-halopyridine, wherein X is Cl, Br, or I.

I. PREPARATION OF COMPOUNDS WHEREIN m IS 1, n IS 0 AND p is 4

SCHEME 10

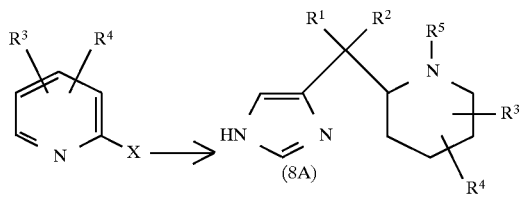

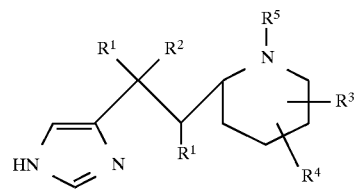
(44)

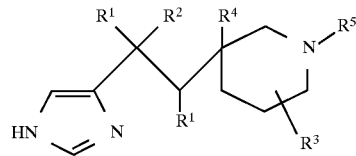
(45)

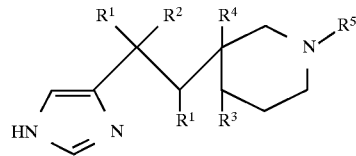
(47)

2-Halopyridine, wherein X is Cl, Br or I, is converted to compound (8A) by following the sequence set forth in Scheme 8.

J. PREPARATION OF COMPOUNDS WHEREIN m IS 2, n IS 0 AND p IS 4: or m IS 2, n IS 1 AND p IS 3

By following the steps in Schemes 1 to 4 with the exception that compound (42)

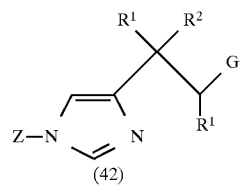

is used instead of compound (2) and compound (43)

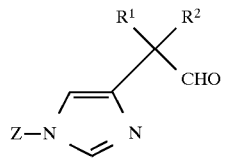
(43)

is used in place of compound (4), compounds (44), (45) and/or (47) are produced. Compound (44) is produced by following Scheme 1 or Scheme 2, and compound (45) and (47) are produced by following Scheme 3 and Scheme 4, respectively. G represents a suitable leaving group such as Br, I, —OSO$_2$—C$_6$H$_4$—CH$_3$, —OSO$_2$—CF$_3$, —OSO$_2$—CH$_3$ and the like. The preparation of compound (42) is described below.

SCHEME 11-PREPARATION OF COMPOUND (42)

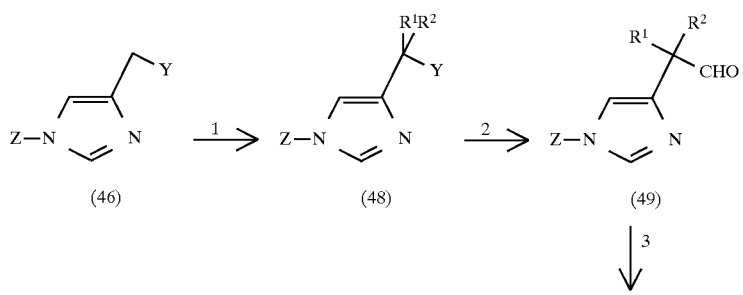

SCHEME 11-PREPARATION OF COMPOUND (42)
-continued

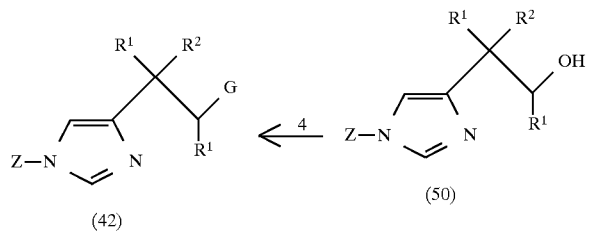

Compound (48) is produced by reacting compound (46) (wherein Y is either CN or $COOR^{10}$ wherein $R^{10}$ is $C_1$ to $C_5$ alkyl) in an organic solvent containing an organic base with $R^1$—L and then with $R^2$—L in accordance with the method set forth in Step 2 of Scheme 6. Preferably, the organic solvent is tetrahydrofuran and the organic base is lithium diisopropylamide. L is a suitable leaving group such as Cl, Br, I, —$OSO_2$—$CF_3$ and the like. Compound (48) is then reduced to compound (49) in THF at a temperature of about −78° to about 70° C. using diisobutylaluminum hydride (when Y is CN) or bis(2-methoxyethoxy)aluminum hydride (when Y is $COOCH_3$; see for example R. Kanazawa & T. Tokoroyama, Synthesis, 526 (1976)) as the reducing agent. Alternatively, the sequence of the preparation of compound (49) from (46) can be switched—i.e., reduction first and then introduction of $R^1$ and $R^2$.

Compound (49) is then reacted with either lithium aluminum hydride (when $R^1$ is H) or $R^1$—Q (when $R^1$ is not H) in tetrahydrofuran at a temperature of about −78° to about 0° C. to produce compound (50). Q represents Li or MgBr. When G represents a halide (i.e., Cl, Br, or I), then compound (42) is produced by either reacting compound (50) with $(C_6H_5)_3P/CG_4$ or $(C_6H_5)_3PG_3$ (see Fiser & Fiser, Reagents for Organic Synthesis, Vol. 1, p1247 (1967)). When G represents —$OSO_2$—$C_6H_4$—$CH_3$, —$OSO_2$—$CH_3$ or —$OSO_2$—$CF_3$, then compound (42) is produced by reacting compound (50) with Cl—$SO_2$—$C_6H_4$—$CH_3$, Cl—$SO_2$—$CH_3$ or Cl—$SO_2$—$CF_3$, respectively, in methylene chloride containing triethylamine (as base) at a temperature of about −78° to about 0° C.

K PREPARATION OF COMPOUNDS WHEREIN m IS 2, n IS 2 AND p is 2

By following the steps in Scheme 5 and Scheme 6, with the exception that compound (42) (see Preparation J) is used instead of compound (2), compound (51) is produced following Scheme 5, and compound (52) is produced following Scheme 6.

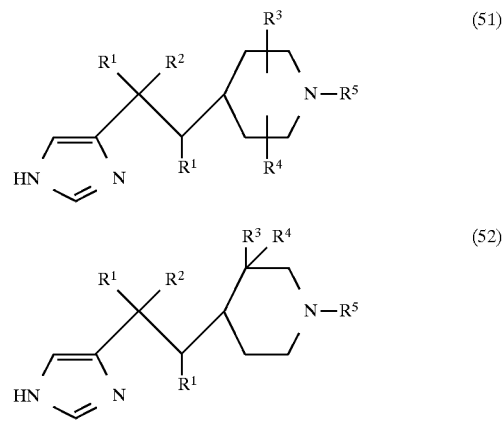

L PREPARATION OF COMPOUNDS WHEREIN DOUBLE BOND INDICATED IN FORMULA 1.0 IS PRESENT AND WHEREIN m IS 1, n IS 2 AND p IS 2

SCHEME 12

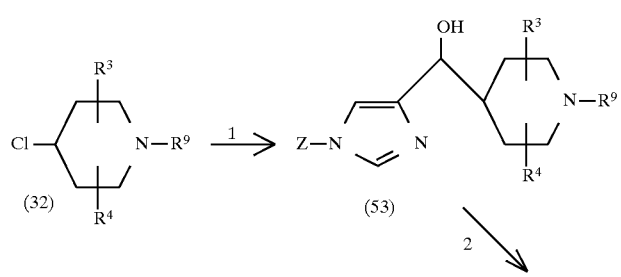

-continued
SCHEME 12

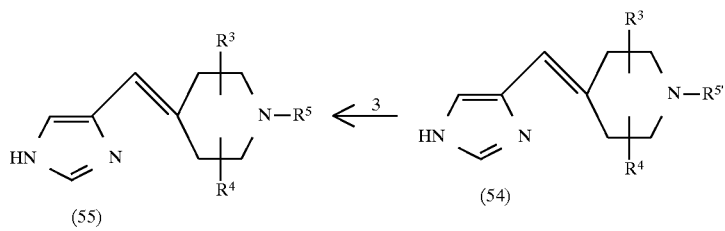

In Step 1 of Scheme 12, compound (32) is reacted with Mg, in accordance with the procedure set forth in Step 1 of Scheme 5, to form the corresponding Grignard reagent. This Grignard reagent is reacted with compound (4)

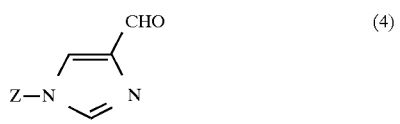  (4)

to form compound (53). The reaction takes place in a suitable organic solvent at a temperature of about –78° to about 20° C. Suitable organic solvents include THF; 1,4-dioxane and the like. Preferably THF is used.

In Step 2 of Scheme 12, compound (53) is converted to compound (54), wherein $R^{5'}$ is H, alkyl, cycloalkyl, benzyl, substituted benzyl, allyl or propargyl group, using an acidic aqueous solution, such as HCl, HBr or the like. The conversion takes place at a temperature of about 50° to about 100° C. Compound (54), wherein $R^{5'}$ is H, is then converted to compound (55) in accordance with Step 4 of Scheme 1.

M. PREPARATION OF COMPOUNDS WHEREIN THE DOUBLE BOND IN FORMULA 1.0 IS PRESENT AND WHEREIN m IS 1, n IS 1 AND p IS 3

SCHEME 13

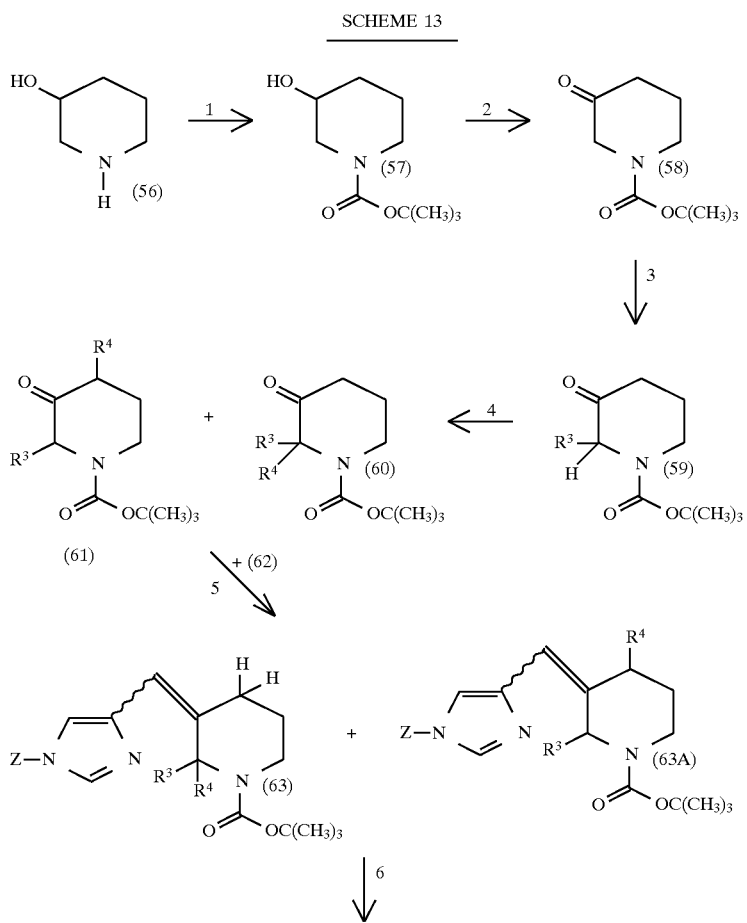

-continued
SCHEME 13

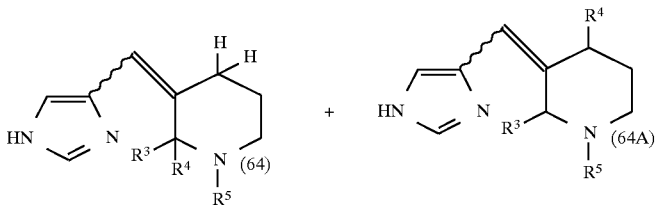

In Step 1 of Scheme 13, compound (57) is produced when compound (56) is reacted with (t-BOC)$_2$O and triethylamine. The reaction is conducted in an organic solvent, such as methylene chloride or DMF, using a temperature within the range of about 0° to about 250° C. (room temperature).

In Step 2 of Scheme 13, compound (58) is produced by treating compound (57) with an oxidizing agent such as pyridinium dichromate or similar oxidizing agent. The oxidation reaction is conducted in an organic solvent, such as methylene chloride, using a temperature of about 25° to about 50° C.

In Step 3 of Scheme 13, compound (59) is produced when the enolate of compound (58) is reacted with R$^3$—L wherein L is a suitable leaving group, such as halogen (e.g., Cl, Br, or I), —OSO$_2$CF$_3$ and the like. The reaction takes place in an organic solvent, such as tetrahydrofuran or benzene, containing a suitable base, such as NaH, KH, LDA, or LiN(Si(CH$_3$)$_3$)$_2$. Preferably, tetrahydrofuran is used as the solvent and LDA is used as the base. The reaction is conducted at a temperature of about 0° to about 80° C.

In Step 4 of Scheme 13, the anion of compound (59) is reacted with R$^4$—L using the same procedure set forth in Step 3 of Scheme 13 in order to produce compound (60) and/or (61).

In Step 5 of Scheme 13, compound (63) or (63A) is obtained when compound (60) or (61) is reacted with compound (62)

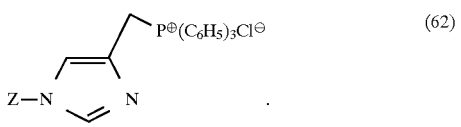

The reaction takes place in an organic solvent, such as tetrahydrofuran, DMF or benzene, containing a suitable base, such as NaH, LDA, or LiN(Si(CH$_3$)$_3$)$_2$. Preferably, tetrahydrofuran is used as the solvent and LDA is used as the base. The reaction is conducted at a temperature of about 0° to about 80° C. Compound (62) is obtained by reacting compound (2A)

with P(C$_6$H$_5$)$_3$ in an organic solvent, such as methylene chloride, CH$_3$CN, tetrahydrofuran and the like, using a temperature of about 25° to about 50° C. In compounds (62) and (2A), Z represents trityl or SEM.

In Step 6 of Scheme 13, compound (64) and (64A) are prepared from compound (63) and (63A), respectively, by following the same procedure set forth in Steps 3 to 5 of Scheme 1.

In the steps of Scheme 13, alkylations (i.e., Steps 3 and 4) are only if desired and R$^3$ and R$^4$ are as defined for Formula 1.0.

N. PREPARATION OF COMPOUNDS WHEREIN THE DOUBLE BOND IN FORMULA 1.0 IS PRESENT AND WHEREIN m IS 1, n IS 2 AND p IS 2

By following the steps in Scheme 13, with the exception that compound (65)

is used instead of compound (56), compound (66) and (66A)

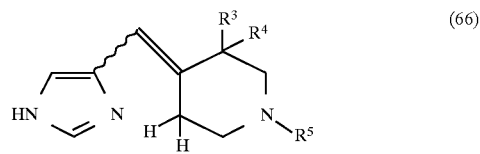

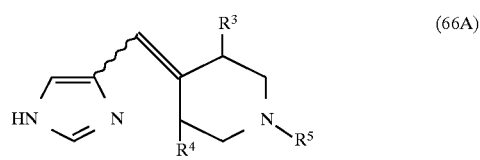

are produced.

In the above processes, certain functional groups may be incompatable with some transformations described herein, and consequently it is sometimes desirable and/or necessary to protect certain groups during the reactions. Certain protecting groups are employed in the above processes but, as those skilled in the art will recognize, other protecting groups may be used in their place. Conventional protecting groups are operable as described in Greene, T. W., and Wuts, P.G.M., "Protective Groups In Organic Synthesis," John Wiley & Sons, New York, 1991; the disclosure of which is incorporated herein by reference thereto. After the reaction or reactions, the protecting groups may be removed by standard procedures.

The compounds of this invention are either agonists or antagonists of the histamine H$_3$ receptor. The binding affinity of the compounds of the invention to the H$_3$ receptor may be demonstrated by the procedure described below:

H$_3$ Receptor Binding Assay

The source of the H$_3$ receptors in this experiment was guinea pig brain. The animals used weighed 400–600 g. The tissue was homogenized using a Polytron in a solution of 50 mM Tris, pH 7.5. The final concentration of tissue in the homogenization buffer was 10% w/v. The homogenates were centrifuged at 1000×g for 10 min. in order to remove clumps of tissue and debris. The resulting supernatants were then centrifuged at 50,000×g for 20 min. in order to sediment the membranes, which were next washed 3 times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 $\mu$g/mL with 0.1% DMSO. Membranes were then added (400 $\mu$g of protein) to the reaction tubes. The reaction was started by the addition of 3 nM [$^3$H]R-$\alpha$-methylhistamine (8.8 Ci/mmol) or [$^3$H]-N-methylhistamine (80 Ci/mmol) and incubated at 30° for 30 min. Bound ligand was separated from unbound ligand by filtration, and the amount of radioactive ligand bound to the membranes was quantitated by liquid scintillation spectrometry. All incubations were performed in duplicate and the standard error was less than 10% in all instances. Compounds that inhibited greater than 70% of the specific binding of radioactive ligand to the receptor were serially diluted to determine a $K_i$ ($\mu$M). The results are given in Table 2.

In Table 2, the compound represented by (a*) is known in the art.

TABLE 2

| COMPOUND | $H_3$ Binding $K_i(\mu M)$ |
|---|---|
| 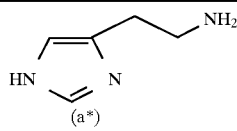 (a*) | 0.014 |
| 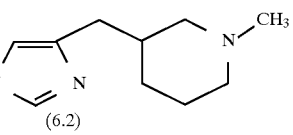 (6.2) | 0.19 |
| 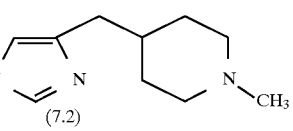 (7.2) | 0.0008 |
| 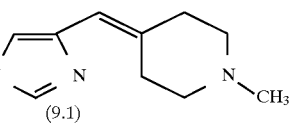 (9.1) | 0.012 |
| 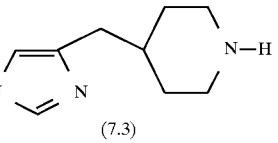 (7.3) | 0.0003 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day preferably 10 to 1000 mg/day, in one to four divided doses to achieve relief of the symptoms. The compounds are non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

A.

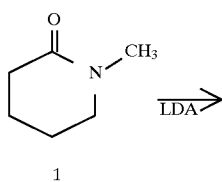

1

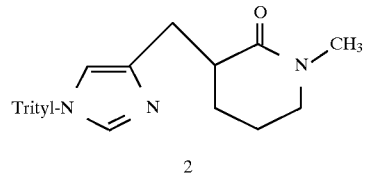

2

To a solution of diisopropylamine (1.078 mL) in anhydrous THF (7 mL) was added n-butyllithium (3.08 mL; 2.5M) dropwise at 0° C.

The resulting solution was stirred at 0° C. for 40 minutes and then was cooled to –23° C. To this mixture was added N-methyl-2-piperidinone (0.80 mL) (1.) the mixture was stirred at –23° C. for 0.5 hour, and then at –78° C. for 1 hour. To the above mixture was added dropwise a solution of 4-chloromethyl-N-trityl-imidazole (2.70 g)

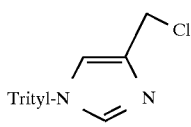

in anhydrous THF (14 mL). The mixture was stirred at –78° C. for 4 hours and then was allowed to warm up to room temperature slowly overnight (16 hours). Water and ethyl acetate were added to the mixture, the resulting mixture was shaken vigorously, the layers separated, and the aqueous layer was extracted with ethyl acetate several times. The combined organic layers were washed with brine, dried over anhydrous sodium sulfate, filtered and evaporated to give the crude product, which was purified by flash chromatography (1% to 2% of ammonia saturated methanol in $CH_2Cl_2$) to give 2 (1.58 g; 52% yield).

B.

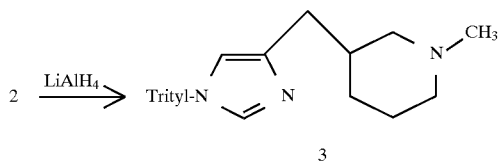

To a solution of 2 (1.54 g) in anhydrous THF (8 mL) was added a 1M solution of lithium aluminum hydride in diethyl ether (11 mL) at room temperature. The resulting solution was stirred for 2 hours and then diethyl ether (100 mL) was added. To the above mixture was carefully added a saturated aqueous sodium sulfate solution until no more hydrogen gas was evolved. The layers were separated, the aqueous layer was basified with $K_2CO_3$ to pH 9 and then extracted with ethyl acetate several times. The combined organic layers were washed with brine, dried over anhydrous $K_2CO_3$, and concentrated to give the crude product which was purified by flash chromatography (5% of ammonia saturated methanol in $CH_2Cl_2$) to give a (1.27 g; 85% yield).

C.

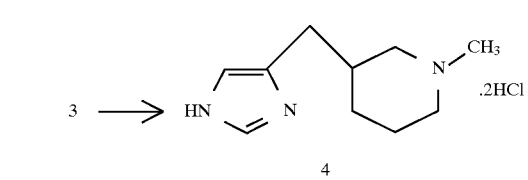

A solution of compound 3 (0.27 9) in a 0.5N HCl solution (20 mL) was heated to 90° C. for 30 minutes. After the mixture was cooled to room temperature, the mixture was extracted with diethyl ether four times. The aqueous layer was separated and concentrated under vacuum to yield the crude product which was recrystallized from $CH_3OH$/diethyl ether to give 4 (0.141 g; 87% yield). MS (CI) 253 (M+1).

EXAMPLE 2

A.

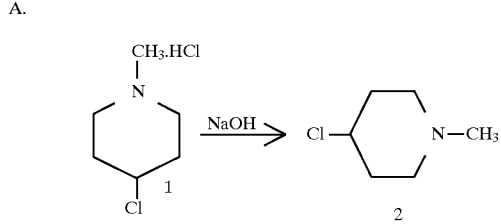

To a solution of 7 g of compound 1 in 35 mL of distilled water at 0° C. was added 5 mL of a 50% aqueous NaOH solution. After 2 minutes of stirring, the mixture was extracted with methylene chloride. The combined organic extracts were washed with brine, dried over anhydrous $Na_2SO_4$ and concentrated. The residue was distilled under vacuum (40° C./18 mmHg) to give 2.7 g of free amine 2 (50% yield).

B.

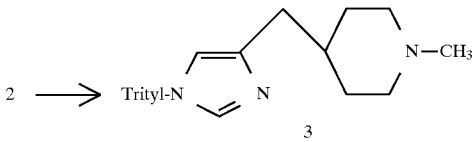

To a mixture of magnesium turnings (0.73 g, 30.2 mmoles) in anhydrous THF (4 mL) at 50° C. was added a solution of N-methyl-4-chloropiperidine 2 (2.7 g, 20.2 mmoles) in 2 mL of anhydrous THF over the course of 1.5 hours. After the addition was complete, the resulting mixture was heated to reflux for 1.5 hours and then it was cooled to –55° C. Copper (I) iodide (0.192 g) was then added and the resulting mixture was stirred at -55° C for 3.5 hours. A solution of N-trityl-4-chloromethylimidazole (4.83 g) in 20 mL of THF was added. The resulting mixture was stirred to $-_{25°}$ C. for 1 hour, at room temperature for 45 minutes, and then it was cooled at –20° C. Aqueous saturated $NH_4Cl$ solution was added to quench the reaction. The mixture was stirred at room temperature until the aqueous layer turned a deep blue color. The organic layer was separated and the aqueous layer was extracted with ethyl acetate. The combined organic solutions were washed with brine, dried over anhydrous Na₂SO₄, filtered and concentrated. The residue was purified by flash chromatography (MeOH/EtOAc) to yield 2.26 g (40% yield) of compound 3.

C.

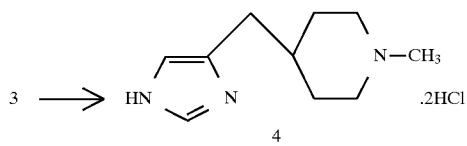

A solution of compound 3 (1.55 g) in 40 mL of 0.5N aqueous hydrochloric acid was heated to reflux for 30 minutes. The mixture was cooled to room temperature and extracted with diethyl ether. The aqueous solution was concentrated and the residue was recrystallized from isopropanol/diethyl ether to give 0.6 g (65% yield) of compound 4. MS (CI) 180 (M+1).

EXAMPLE 3

A.

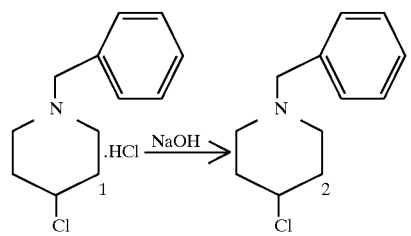

B.

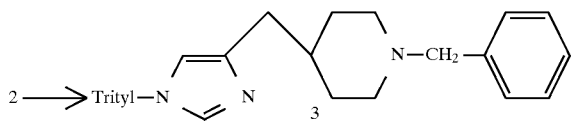

In a manner similar to that described in Example 2, Steps A and B. N-benzyl-4-chloropiperidine (1) is converted to compound 3.

C.

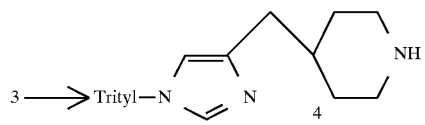

To a solution of a (1.49 g) in 20 mL of anhydrous methanol was added 0.95 g of ammonium formate (NH₄COO), and 1.49 g of 10% Pd/C. The mixture was refluxed under nitrogen for 40 minutes, cooled to room temperature, and then filtered through a pad of celite. The filtrate was concentrated, and the residue was purified by flash chromatography on silica gel to give 0.81 g (66% yield) of compound 4.

D.

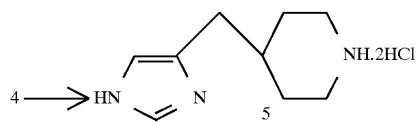

A solution of compound 4 (0.31 g) in 25 mL of 1N aqueous hydrochloric acid was heated to reflux for one hour. The mixture was cooled to room temperature and extracted with diethyl ether. The aqueous solution was concentrated and the residue was recrystallized from isopropanol/diethyl ether to give 0.16 g (64% yield) of compound 5. MS (CI) 166 (M+1).

EXAMPLE 4

A.

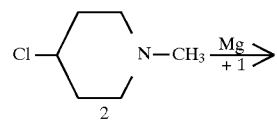

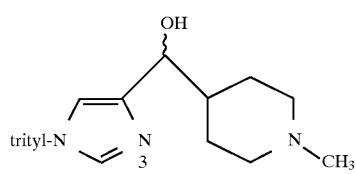

To a mixture of magnesium turnings (0.73 g) in anhydrous THF (4mL) at 50° C. was added a solution of N-methyl-4-chloropiperidine (2) (2.7 g) in 2 mL of anhydrous THF over the course of 1.5 hours. After the addition was complete, the resulting mixture was heated to reflux for an additional 1.5 hours and then the mixture was cooled to 0° C. A solution of N-tritylimidazoylcarboxaldehyde (1)

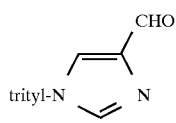

(6.83 g of 1 in 50 mL of THF) was added to the above Grignard reagent solution. The reaction mixture was stirred for 1 hour at 0° C. and then quenched with water. The organic layer was separated and the aqueous layer was extracted with ethyl acetate. The combined organic layers were washed with brine, dried over anhydrous sodium sulfate and concentrated. The residue was purified by flash chromatography on silica gel (eluting solvents: 1 to 10% ammonia saturated methanol in methylene chloride) to give 6.9 g (77% of compound 3).

B.

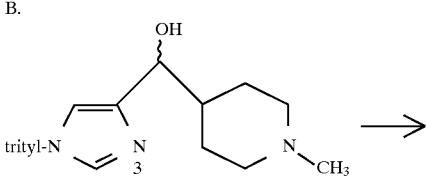

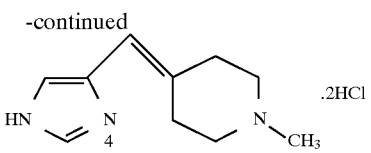

A solution of 1.6 g of compound a in 40 mL of 85% sulfuric acid was stirred at room temperature for 24 hours. After the solution was cooled to 0° C., the reaction mixture was basified with KOH to pH=9. The mixture was filtered and the filtrate was concentrated to approximately ⅓ volume. The resulting solution was extracted with 2:1 ethyl acetate/dichloromethane. The combined organic extracts were dried over anhydrous potassium carbonate, filtered, and concentrated to give an oil which was purified by preparative TLC (10% to 20% of ammonia saturated methanol in dichloromethane) to yield the free amine of 4. The free amine of 4 was dissolved in dilute HCl and pumped dry to give 0.303 g (33%) of compound 4. MS (CI) 178 (M+1).

The following are examples of pharmaceutical dosage forms which contain a compound of the invention. As used therein, the term "active compound" is used to designate the compound

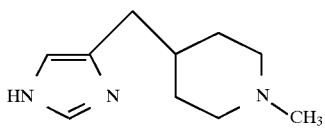

The scope of the invention in its pharmaceutical composition aspect is not to be limited by the examples provided, since any other compound of structural formula 1.0 can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredients | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

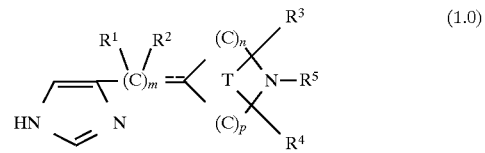

or a pharmaceutically acceptable salt or solvate thereof, wherein:

(A) m is 1;

(B) n and p are integers and are each independently selected from the group consisting of: 0, 1, 2, 3, and 4 such that the sum of n and p is 4 and T is a 6-membered ring;

(C) $R^3$ and $R^4$ are each independently bound to the same or different carbon atom of ring T such that there is only one $R^3$ group and one $R^4$ group in ring T, and each $R^1$, $R^2$, $R^3$, and $R^4$ is independently selected from the group consisting of:
  (1) H;
  (2) $C_1$ to $C_6$ alkyl;

(D) $R^5$ is selected from the group consisting of:
  (1) H;
  (2) $C_1$ to $C_{20}$ alkyl;
  (3) $C_3$ to $C_6$ cycloalkyl;
  (4) —C(O)OR$^{7'}$; wherein R$^{7'}$ is the same as $R^7$ defined below except that R$^{7'}$ is not H;
  (5) —C(O)R$^7$;
  (6) —C(O)NR$^7$R$^8$;
  (7) allyl;
  (8) propargyl; and
  (9) —(CH$_2$)$_q$—R$^6$, wherein q and $R^6$ are as defined above, and when q is equal to 1, then $R^6$ is not OH or SH;

(E) $R^7$ and $R^8$ are each independently selected from the group consisting of: H, $C_1$ to $C_6$ alkyl, and $C_3$ to $C_6$ cycloalkyl;

(F) the dotted line (------) represents a double bond that is optionally present when m is 1, and n is not 0, and p is not 0, and when said double bond is present then $R^2$ is absent.

2. The compound of claim 1 wherein $R^5$ is selected from the group consisting of H and $C_1$ to $C_{15}$ alkyl, and $R^1$ to $R^4$ are each independently selected from the group consisting of: H, $C_1$ to $C_6$ alkyl, and $-(CH_2)_q-R^6$ wherein $R^6$ is phenyl.

3. The compound of claim 2 wherein $R^5$ is selected from the group consisting of H and $C_1$ to $C_6$ alkyl, and $R^3$ and $R^4$ are each independently selected from the group consisting of H and methyl.

4. The compound of claim 3 wherein $R^5$ is selected from the group consisting of H and methyl.

5. The compound of claim 1 wherein said compound is selected from the group consisting of compounds having the formula:

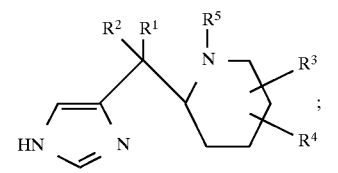 (5.0)

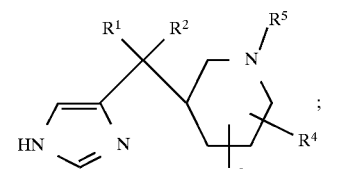 (6.1)

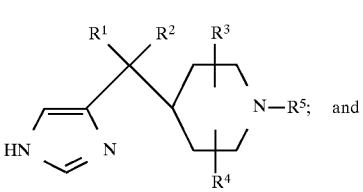 (7.1)

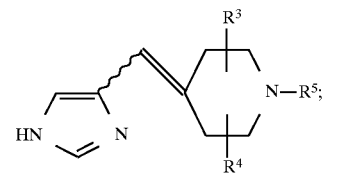 (9.1)

wherein $R^1$ to $R^5$ are as defined for Formula 1.0.

6. The compound of claim 1 wherein said compound is selected from the group consisting of compounds having the formula:

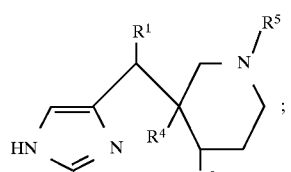 (6.0)

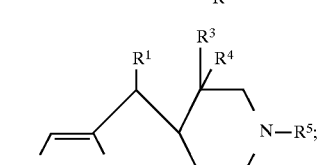 (7.0)

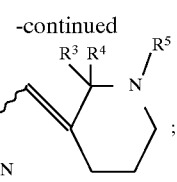 (8.0)

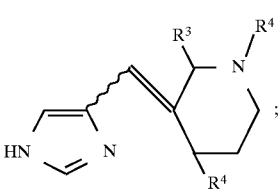 (8.1)

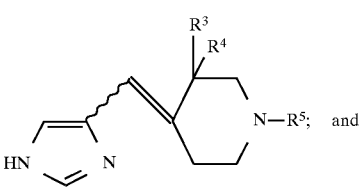 (9.0) and

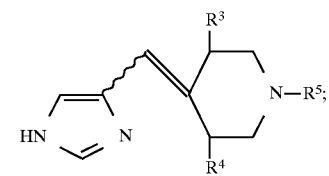 (9.2)

wherein $R^1$ to $R^5$ are as defined for Formula 1.0.

7. The compound of claim 1 wherein $R^5$ is selected from the group consisting of: H, $C_1$ to $C_6$ alkyl, $-C(O)OR^7$, $-C(O)R^7$, $-C(O)NR^7R^8$, and $-(CH_2)_q-R^6$ wherein $R^6$ is phenyl.

8. The compound of claim 7 wherein $R^2$ is H.

9. The compound of claim 8 wherein $R^5$ is selected from the group consisting of H and $C_1$ to $C_6$ alkyl, and $R^4$ is H.

10. The compound of claim 1 wherein said compound is selected from the group consisting of compounds having the formula:

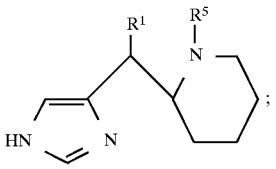 (5.3)

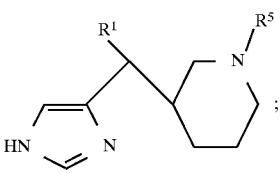 (6.4)

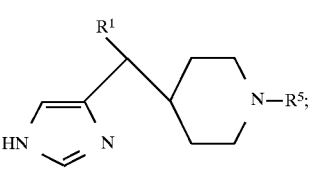 (7.4)

-continued

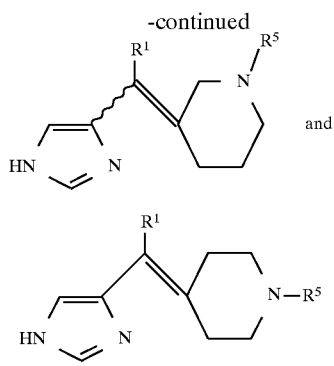
(8.4)

and

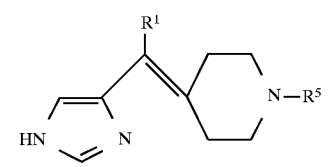
(9.4)

wherein $R^1$ is selected from the group consisting of: H and $C_1$ to $C_6$ alkyl, and $R^5$ is selected from the group consisting of: H, $C_1$ to $C_6$ alkyl, —C(O)OR', —C(O)R$^7$, —C(O)NR$^7$R$^8$, and —(CH$_2$)$_q$R$^6$ wherein $R^6$ is phenyl.

11. The compound of claim 10 wherein $R^5$ is selected from the group consisting of: H and $C_1$ to $C_6$ alkyl.

12. The compound of claim 11 wherein $R^1$ and $R^5$ are independently selected from the group consisting of: H and methyl.

13. The compound of claim 1 wherein said compound is selected from the group consisting of:

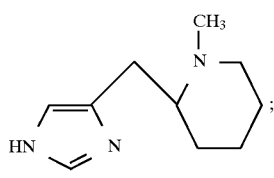
(5.1)

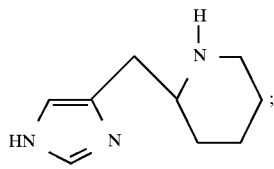
(5.2)

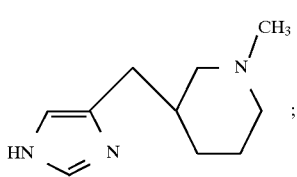
(6.2)

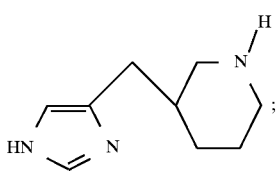
(6.3)

-continued

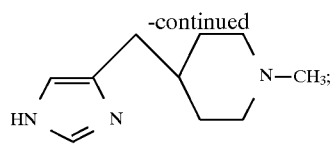
(7.2)

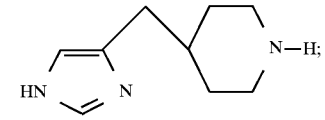
(7.3)

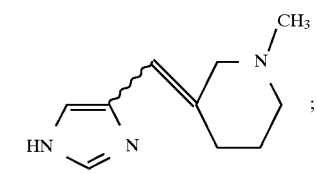
(8.2)

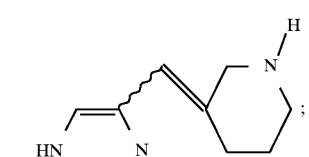
(8.3)

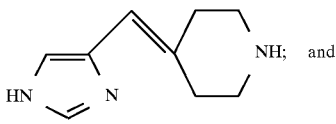
(9.2)

and

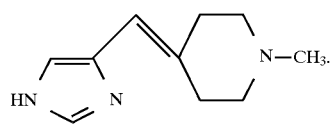
(9.3)

14. A compound of the formula:

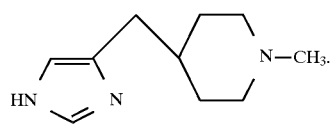
(7.2)

15. A compound of the formula:

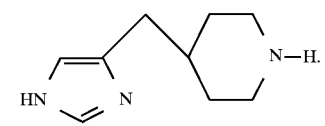
(7.3)

16. A pharmaceutical composition, comprising a pharmaceutically acceptable carrier and a therapeutically effective amount of a Compound of claim 1.

* * * * *